(12) United States Patent
Dhainaut et al.

(10) Patent No.: US 6,518,439 B1
(45) Date of Patent: Feb. 11, 2003

(54) METHOD FOR PREPARING VITAMIN E

(75) Inventors: Jildaz Dhainaut, Lyons (FR); Thierry Durand, Antony (FR)

(73) Assignee: Aventis Animal Nutrition, S.A., Antony (FR)

( * ) Notice: Subject to any disclaimer, the term of this patent is extended or adjusted under 35 U.S.C. 154(b) by 0 days.

(21) Appl. No.: 09/787,264

(22) PCT Filed: Sep. 15, 1999

(86) PCT No.: PCT/FR99/02196

§ 371 (c)(1),
(2), (4) Date: May 14, 2001

(87) PCT Pub. No.: WO00/17185

PCT Pub. Date: Mar. 30, 2000

(30) Foreign Application Priority Data

Sep. 18, 1998 (FR) .......................................... 98 11679

(51) Int. Cl.⁷ ............................................. C07D 311/72
(52) U.S. Cl. ..................... 549/410; 549/411; 549/412
(58) Field of Search ................................. 549/410, 411, 549/412

(56) References Cited

U.S. PATENT DOCUMENTS 6,005,122 A * 12/1999 Baldenius et al. .......... 549/410
6,020,505 A * 2/2000 Hirose et al. ............... 549/411

FOREIGN PATENT DOCUMENTS

| JP | 60054380 | * | 3/1985 |
| JP | 58171248 | * | 4/1985 |

* cited by examiner

Primary Examiner—Joseph K. McKane
Assistant Examiner—Andrea D. Small
(74) Attorney, Agent, or Firm—Connolly Bove Lodge & Hutz LLP

(57) ABSTRACT

The invention concerns a novel method for preparing vitamin E. More particularly, it concerns a novel method for the condensation of Arimethylhydroquinone and isophytol.

11 Claims, No Drawings

METHOD FOR PREPARING VITAMIN E

This application is a 371 of PCT/FR99/02196 filed on Sep. 15, 1999.

The present invention relates to a novel process for the preparation of vitamin E. It relates more particularly to a novel process for the condensation of trimethylhydroquinone and isophytol.

It is known, for example according to Japanese Patents No. 60064977, No. 53144574 and No. 53015381, to condense isophytol with trimethylhydroquinone in the presence of a Lewis acid, restricted to zinc chloride, in the presence of an inorganic acid chosen from halogenated acids and polyphosphoric acid in a solvent composed of methylene chloride and acetic acid.

It is also known, from Japanese Patents No. 59190987 and No. 48072168, to condense trimethylhydroquinone with isophytol in the presence of a catalyst based on zinc chloride and of an acid chosen from hydrochloric acid or trichloroacetic acid; the reaction being carried out in a solvent composed of an acetyl ester and in particular of isopropyl acetate.

Finally, it is known, from Japanese patent No. 48072167, to condense isophytol with trimethylhydroquinone under the same conditions as above but removing the water of the reaction as it is formed during the condensation. Japanese Patent No. 6226976, which carries out the reduction of trimethylhydroquinone and the condensation with isophytol in the same solvent as above, that is to say isopropyl acetate, eliminates the presence of water between the two stages so as to avoid the presence of water during the final condensation of trimethylhydroquinone with isophytol.

The present reaction can be represented schematically in the following way:

as an alkane, is used. The maximum amount of water which can be used without harming the reaction yield and without distilling off the water formed during the reaction is limited to 1.5 mol of water per mole of isophytol. Under these conditions, the influence of the amount of zinc chloride used was not studied.

It has transpired that, when the process described previously is carried out, that is to say when the catalysis with zinc chloride was carried out in the absence of water and in a polar solvent, such as esters, there was a significant lose of TMHQ by transesterification with the solvent. The present invention has made it possible to overcome this problem and has made it possible to carry out the condensation of TMHQ with isophytol in a polar solvent of the ester type and in the presence of water.

The present invention thus consists in carrying out the condensation of a phytol with trimethylhydroquinone in a polar solvent of the ester type and in the presence of a Bronsted acid and of a zinc halide, characterized in that the reaction is carried out in the presence of an amount of water of between 0.7 molar eq. and 2 molar eq. with respect to the number of moles of zinc halide and in the presence of an amount of zinc halide of greater than 0.3 molar equivalent with respect to the phytol.

The presence of this amount of water has numerous advantages:
  it makes it possible to increase the reaction yield by approximately 4%,
  it makes it possible to recycle the zinc halide,
  at equivalent stoichiometry for TMHQ and phytol, the presence of water increases the yield,
  it prevents the esterification of TMHQ by the solvent.

Furthermore, in the case of solvents from the family of the esters, in contrast with the case of the hydrocarbons dis-

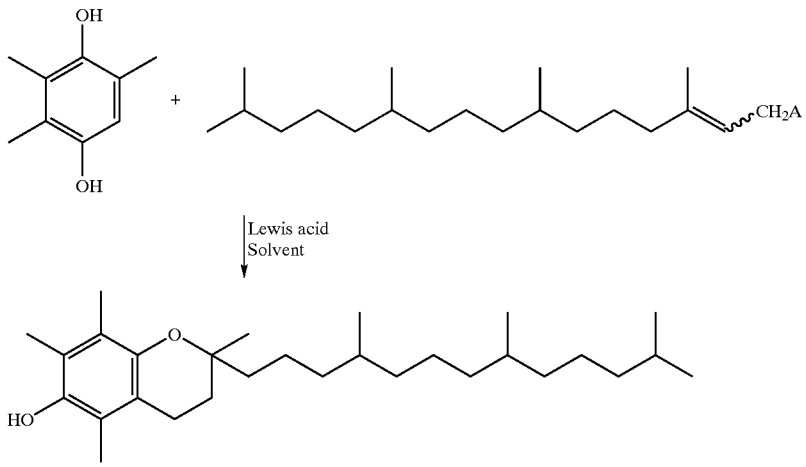

in which scheme A represents a halogen atom, a hydroxyl group or an acetoxy group.

It has transpired, entirely surprisingly, that, if it is desired to restrict the consumption of TMHQ to 1 molar eq. with respect to isophytol, the presence of water in the condensation stage has a favourable effect on the reaction, contrary to that suggested by all of this prior art. The water prevents side reactions of TMHQ at the beginning of the running in of isophytol.

Furthermore, it is known, according to Patent EP 0 850 937, that it is possible to condense TMHQ with isophytol in the presence of water provided that a nonpolar solvent, such closed in Patent EP 0 850 937, the presence of water requires the use of amounts of zinc halides of greater than 0.3 molar equivalent with respect to phytol, so as:
  to retain a yield >92%
  to accelerate the kinetics of the reaction.

The phytol is chosen from isophytol or a phytyl halide, such as phytyl bromide, phytyl chloride or phytyl acetate.

The reaction is carried out in particular in the presence of a Bronsted acid chosen from hydrochloric acid or sulphuric acid. It is preferable to use hydrochloric acid.

The reaction is carried out in the presence of a polar solvent which makes it possible to dissolve trimethylhydroquinone and the phytol used. Mention may be made, among polar solvents which may be used, of esters and among these of ethyl, propyl, isopropyl, butyl or isobutyl acetate; acetates having a longer chain are not preferred although they can be used; the viscosity of the solvent simply increases with the length of the chain, which is not very favourable to the reaction. Esters of longer organic acids than the acetates can also be used, in particular esters of propionic, butyric or isobutyric, valeric or isovaleric acid, but, as in the case of the acetates, the increase in the length of the chain increases the viscosity of the medium, which is not always favourable to the reaction. It is preferable, among all these esters, to use isopropyl acetate.

The presence of water in the reaction medium, which improves the condensation yield, leads in some cases to the presence of a two-phase system. In this case, it is advantageous to add an organic acid chosen from acetic acid, propionic acid or butyric acid in order to prevent the phases from separating. It is preferable to use the acid corresponding to the ester used as solvent. Thus, when an acetate is used, it is preferable to add acetic acid.

The amount of organic acid added corresponds to approximately 3 to 20 times the amount by weight of water present in the medium.

The catalyst used to promote the condensation is chosen from zinc halides. It is preferable to use zinc chloride. It is advantageous also to use a Bronsted acid chosen from hydrochloric acid or sulphuric acid.

According to a better way of implementing the invention, the catalyst is used according to a ratio of approximately 0.7 to 1.2 equivalents per mole of phytol.

The advantage of using this amount of Lewis acid with respect to the prior art, which uses less thereof, is:

to increase the reaction rate, to improve the selectivity of the condensation.

The molar ratio of the hydroquinone to the phytol is preferably between 1 and 1.5 and it is highly preferably between 1 and 1.2. The Bronsted acid is preferably used according to a molar amount of between 4% and 16% with respect to the number of moles of phytol.

For a better implementation of the invention, it is preferable to operate at a temperature of between 55° C. and 75° C.

The α-tocopherol obtained is separated from the reaction medium by liquid/liquid extraction.

The following stage of the process for the preparation of vitamin E, when it is provided in the acetate form, consists in carrying out the acetylation of the α-tocopherol.

This stage is carried out according to a novel method which consists in acetylating the α-tocopherol with acetic anhydride in the absence of any solvent, that is to say neat.

The acetylation is carried out in the presence of a catalyst composed of an inorganic acid chosen from sulphuric acid or phosphoric acid or of an alkaline acetate.

It has been discovered that it is preferable to employ phosphoric acid or sodium acetate as it is possible, with these catalysts, to completely avoid colouring the reaction medium during the acetylation. The tocopheryl acetate obtained is even lighter than the starting tocopherol. It is preferable to use a molar ratio of the acetic anhydride to the tocopherol of between 1 and 1.8. Use if preferably made of 0.7 to 2 molar % of acid as acetylation catalyst when the latter is sulphuric acid, 1 to 2 molar % when the acetylation catalyst is phosphoric acid and 5 to 10 molar % when the acetylation catalyst is sodium acetate.

The present invention also relates to a complete process for the preparation of vitamin E from trimethylbenzoquinone, the entire process being carried out in the same solvent, which is a good solvent for trimethylbenzoquinone, for trimethylhydroquinone and for the phytol. This solvent is in particular a polar solvent, preferably an ester and highly preferably isopropyl acetate.

It consists, in a first stage, in carrying out a hydrogenation of trimethylbenzoquinone with a hydrogenation catalyst, preferably a supported catalyst, chosen from palladium and platinum. It is preferable to use palladium supported on charcoal.

The second stage consists, after filtration so as to remove the catalyst, in carrying out the condensation of the trimethylhydroquinone obtained in the first stage with the phytol under the conditions described above and in particular in the presence of a zinc halide, of a Bronsted acid and of water and very particularly in the presence of zinc chloride, of hydrochloric acid and of water. At the end of the reaction, the catalyst is extracted with water and this aqueous phase is concentrated, in particular from 80 wt % to 91 wt % of $ZnCl_2$, so as to leave at most, including the water from the Bronsted acid, only two moles of water per mole of zinc halide recycled to the second stage of the process.

The organic phase is then preferably concentrated to dryness, so as to remove the reaction solvent and its possible by-products, and then acetylated neat as described above.

The process for the extraction of vitamin E acetate is subsequently carried out conventionally and in a way known to a person skilled in the art. The medium is extracted with a solvent which is immiscible or virtually immiscible with water, then washed with an acid solution, so as to hydrolyse the remaining acetic anhydride, and then washed in alkaline medium, to deacetylate the TMHQ acetates. The aqueous phase comprising the alkaline salt of TMHQ is isolated by a two-phase separation, this phase is acidified and the TMHQ is extracted with the reaction solvent, that is to say the ester, which allows it to be recycled to the condensation stage.

The invention will be more fully described with the help of the following examples, which should not be regarded as limiting the invention.

EXAMPLES

Preparation of TMHQ in Solution by Hydrogenation

Example 1

3.1 g of Pd/C (3%, 52% $H_2O$) and 3550 g of IPAC are charged to an 8 l hydrogenation reactor rendered inert beforehand with nitrogen. The reactor is placed under 0.5 bar of hydrogen with stirring. The medium is heated to 80° C. and is maintained at this temperature for 10 minutes.

The reactor is subsequently pressurized to 2 bar of hydrogen. Hydrogenation is carried out semi-continuously by simultaneous addition of 96.5% w/w TMBQ (total charge= 700.3 g) and of hydrogen, so as to remain at 80° C. and under 2 bar of hydrogen. The end of the reaction is detected by the fall in the hydrogen flow rate.

The reaction medium is degassed and then purged with nitrogen. The reaction medium is filtered while hot under nitrogen pressure. The solution of 708.2 g of TMHQ in IPAC is obtained which is ready for use in the condensation reaction. The hydrogenation yield is 99.8%.

TMHQ/Isophytol Condensation Reactions in the Absence of Water

Example 2

A hot solution of 76 g of TMHQ in IPAC comprising 16% w/w of IPAC is charged with stirring to a 1 l reactor. This solution is concentrated with stirring to 38% w/w by distillation of IPAC at 45° C. under vacuum. 50.1 g of 98% w/w $ZnCl_2$, dissolved in 72 g of acetic acid under warm conditions, are added to the suspension obtained, followed by 4 g of 92% w/w of sulphuric acid. The reaction medium is heated to 75° C. 162 g of 91.5% w/w isophytol are then run in over 43 min. After the isophytol has finished being run in, the reaction is maintained at 75° C. for 60 min. 100 g of water are charged with stirring and the mixture is subsequently separated by settling. The volatile products are removed from the organic phase by distillation at 75° C. under vacuum. 1 g of 92% w/w sulphuric acid is charged at 75° C. and then 88.5 g of 98% w/w acetic anhydride are run in at this temperature over 10 min. The reaction medium is heated to 105° C. over 20 min and then rapidly cooled to 35° C. 1200 g of hexane are charged with stirring, followed by 71 g of water. The two phases are separated by settling. The organic phase is again washed with 71 g of water. The organic phase is evaporated on a rotary evaporator at 60° C. under vacuum for 2 h.

254.8 g of crude 84.2% w/w tocopheryl acetate (Toco) are obtained (yield=90.9%).

The procedure of Example 3 is identical to that of Example 2. only the running-in time changes 84 min). The parameters are shown in Table 1.

solution is concentrated with stirring to 38% w/w by distillation of IPAC at 45° C. under vacuum. 50.1 g of 98% w/w $ZnCl_2$, dissolved in 72 g of acetic acid under hot conditions, are added to the suspension obtained, followed by 8.1 g of 36% w/w hydrochloric acid. The reaction medium is heated to 75° C. 161.6 g of 91.6% w/w isophytol are then run in over 47 min. After the isophytol has finished being run in, the reaction is maintained at 75° C. for 60 min. 100 g of water are charged with stirring and the mixture is subsequently separated by settling. The volatile products are removed from the organic phase by distillation at 75° C. under vacuum. 1.1 g of 92% w/w sulphuric acid are charged at 75° C. and then 88.6 g of 98% w/w acetic anhydride are run in at this temperature over 10 min. The reaction mixture is heated to 105° C. over 30 min and then rapidly cooled to 35° C. 120 g of hexane are charged with stirring, followed by 70 g of water. The two phases are separated by settling. The organic phase is again washed with 70 g of water. The

TABLE 1

Influence of the absence of water.

| Example | Maintenance time (min) | AcOH (g) | $ZnCl_2$ (eq)* | Acid (eq) | T (° C.) | $H_2O$ (g) | Total $H_2O$** (mol/mol $ZnCl_2$) | Toco assay (%) | Toco Yd (% pure/pure) |
|---|---|---|---|---|---|---|---|---|---|
| 2 | 60 | 72 | 0.72 | $H_2SO_4$ (0.08) | 75 | 0 | 0.05 | 84.2 | 90.9 |
| 3 | 60 | 72 | 0.72 | $H_2SO_4$ (0.08) | 75 | 0 | 0.05 | 81.9 | 87.2 |

TMHQ/Isophytol = 1 molar eq.
*the equivalents are in moles with respect to the number of moles of isophytol
**total $H_2O$ = $H_2O$ + $H_2O$ present in 92% $H_2SO_4$.

TMHQ/Isophytol Condensation Reactions in the Presence of Water

Reactions with Acid=36% HCl without Addition of Additional Water

Example 4

A hot solution of 76 g of TMHQ in IPAC comprising 16% w/w of IPAC is charged with stirring to a 1 l reactor. This organic phase is evaporated on a rotor evaporator at 60° C. under vacuum for 2 h.

258 g of crude 86.4% w/w tocopheryl acetate (Toco) are obtained (yield=94.3%).

The procedures of Examples 5 and 6 are identical to that of Example 4. The parameters modified in the examples are specified in Table 2.

TABLE 2

Influence of the presence of water.

| Example | Maintenance time (min) | AcOH (g) | $ZnCl_2$ (eq)* | Acid (eq) | T (° C.) | $H_2O$ added (g) | Total $H_2O$** (mol/mol $ZnCl_2$) | Toco assay (%) | Toco Yd (% pure/pure) |
|---|---|---|---|---|---|---|---|---|---|
| 4 | 60 | 72 | 0.72 | 36% HCl (0.16) | 75 | 0 | 0.75 | 86.4 | 94.3 |
| 5 | 60 | 72 | 0.72 | 36% HCl (0.16) | 75 | 0 | 0.75 | 87.8 | 93.4 |
| 6 | 90 | 47 | 0.45 | 36% HCl (0.09) | 62 | 0 | 0.75 | 89.5 | 97 |

TMHQ/Isophytol = 1 molar eq.
*the equivalents are in moles with respect to the number of moles of isophytol
**total $H_2O$ = $H_2O$ + $H_2O$ present in 36% HCl.

TMHQ/Isophytol Condensation Reactions in the Presence of Water
Reactions with Acid=36% HCl or 92% $H_2SO_4$ with Addition of Water
Influence of the Water Content and of the $ZnCl_2$ Stoichiometry

Example 7

A hot solution of 76 g of TMHQ in IPAC comprising 16% w/w of IPAC is charged with stirring to a 1 l reactor. This solution is concentrated with stirring to 38% w/w by distillation of IPAC at 45° C. under vacuum. 50.1 g of 98% w/w $ZnCl_2$, dissolved in 72 g of acetic acid under warm conditions, 4.28 g of 92% w/w sulphuric acid and 5 g of water are added to the suspension obtained. The reaction mixture is heated to 75° C. 162 g of 91.5% w/w isophytol are then run in over 40 min. After the isophytol has finished being run in, the reaction is maintained at 75° C. for 60 min. 200 g of water are charged with stirring and the mixture is subsequently separated by settling. The volatile products are removed from the organic phase by distillation at 75° C. under vacuum. 1.1 g of 92% w/w sulphuric acid are charged at 75° C. and then 88.5 g of 98% w/w acetic anhydride are run in at this temperature over 10 min. The reaction medium is heated to 105° C. over 30 min and is then rapidly cooled to 35° C. 200 g of hexane are charged with stirring, followed by 50 g of water. The two phases are separated by settling. The organic phase is again washed with 30 g of water. The organic phase is evaporated on a rotary evaporator at 60° C. under vacuum for 2 h.

253.2 g of crude 88.2% w/w tocopheryl acetate (Toco) are obtained (yield=94.6%).

The procedures of Examples 8 to 15 are identical to that of Example 7. The sulphuric acid is sometimes replaced by hydrochloric acid. The parameters modified in the examples are specified in Table 3.

TMHQ/Isophytol Condensation Reactions in the Presence of Water
Influence of the TMHQ and $ZnCl_2$ Stoichiometry

Example 16

A hot solution of 76 g of TMHQ in IPAC comprising 16% w/w of IPAC is charged with stirring to a 1 l reactor. This solution is concentrated with stirring to 38% w/w by distillation of the IPAC at 45° C. under vacuum. 49.8 g of 98% w/w $ZnCl_2$, dissolved in 45 g of acetic acid under warm conditions, 4.7 g of 36% w/w hydrochloric acid and then 4.8 g of water are added to the suspension obtained. The reaction mixture is heated to 72° C. 160.5 g of 92.2% w/w isophytol are then run in over 20 min. After the isophytol has finished being run in, the reaction is maintained at 72° C. for 40 min. 100 g of water are charged with stirring and the mixture is subsequently separated by settling. A second washing is carried out with 60 g of water. The volatile products are removed from the organic phase by distillation at 75° C. under vacuum. 0.6 g of 92% w/w sulphuric acid are charged at 85° C. and then 68 g of 92% w/w acetic anhydride are run in at this temperature over 6 min. The reaction medium is maintained at this temperature for 60 min and then rapidly cooled to 35° C. 240 g of hexane are charged with stirring, followed by 220 g of water and by 9 g of 92% w/w $H_2SO_4$. The two phases are separated by settling. The organic phase is then washed with a mixture of 100 g of water and 12 g of 50% NaOH. The organic phase is evaporated on a rotor evaporator at 60° C. under vacuum for 2 h.

After evaporation of partial purification, 232.7 g of 94.8% w/w tocopheryl acetate (Toco) are obtained (yield=93.3%).

The residual TMHQ is recovered by acidification of the alkaline aqueous phase with 92% w/w $H_2SO_4$ and then extraction with IPAC. The solution of recovered TMHQ in IPAC can be recycled in the TMHQ/Isophytol condensation.

The procedures of Examples 17 to 19 are identical to that of Example 16. The parameters modified in the examples are specified in Table 4.

TABLE 3

Influence of the water content and of the $ZnCl_2$ stoichiometry.

| Example | Maintenance time (min) | AcOH (g) | $ZnCl_2$ (eq)* | Acid (eq) | T (° C.) | $H_2O$ (g) | Total $H_2O$** (mol/mol $ZnCl_2$) | Toco assay (%) | Toco Yd (% pure/pure) |
|---|---|---|---|---|---|---|---|---|---|
| 7 | 60 | 72 | 0.72 | $H_2SO_4$ (0.08) | 75 | 5 | 0.75 | 88.2 | 94.6 |
| 8 | 60 | 0 | 0.72 | $H_2SO_4$ (0.04) | 75 | 11 | 1.65 | 86.6 | 93.8 |
| 9 | 120 | 18 | 0.18 | 36% HCl (0.08) | 75 | 0 | 1.5 | 83.2 | 90.1 |
| 10 | 40 | 36 | 0.36 | $H_2SO_4$ (0.04) | 75 | 2.5 | 0.75 | 93.4*** | 95.5 |
| 11 | 60 | 66 | 0.63 | $H_2SO_4$ (0.063) | 62 | 4.3 | 0.75 | 89.6 | 98.4 |
| 12 | 60 | 47 | 0.45 | $H_2SO_4$ (0.045) | 62 | 3.07 | 0.75 | 89.4 | 98.3 |
| 13 | 80 | 40 | 0.72 | 36% HCl (0.15) | 62 | 2.8 | 1.12 | 90.6 | 97.5 |
| 14 | 80 | 0 | 0.45 | 36% HCl (0.09) | 62 | 3.07 | 1.5 | 88.3 | 95.4 |
| 15 | 90 | 45 | 0.72 | 36% HCl (0.09) | 62 | 9.6 | 1.88 | 87.8 | 95.8 |

TMHQ/Isophytol = 1 molar eq.
*the equivalents are in moles with respect to the number of moles of isophytol
**total $H_2O$ = $H_2O$ + $H_2O$ present in the acid
***After partial purification

TABLE 4

Influence of the water content and of the ZnCl$_2$ stoichiometry.

| Example | Maintenance time (min) | AcOH (g) | TMHQ (eq) | ZnCl$_2$ (eq)* | Acid (eq) | T (° C.) | H$_2$O (g) | Total H$_2$O** (mol/mol ZnCl$_2$) | Toco assay (%) | Toco Yd (% pure/pure) |
|---|---|---|---|---|---|---|---|---|---|---|
| 16 | 40 | 45 | 1.01 | 0.72 | 36% HCl (0.09) | 72 | 4.8 | 1.12 | 94.7*** | 93.3 |
| 17 | 40 | 45 | 1.05 | 0.72 | 36% HCl (0.09) | 75 | 4.8 | 1.12 | 95*** | 95.7 |
| 18 | 20 | 45 | 1.15 | 0.72 | 36% HCl (0.09) | 75 | 4.8 | 1.12 | 93.2*** | 96.2 |
| 19 | 40 | 62 | 1.15 | 1 | 36% HCl (0.09) | 75 | 7.6 | 1.12 | 96.4*** | 98 |

*the equivalents are in moles with respect to the number of moles of isophytol
**total H$_2$O = H$_2$O + H$_2$O present in the acid
***After partial purification TMHQ/Isophytol Condensation Reactions in the Presence of Water
Recycling of ZnCl$_2$

Example 20

A hot solution of 76 g of TMHQ in IPAC comprising 16% w/w of IPAC is charged with stirring to a 1 l reactor. This solution is concentrated with stirring to 38% w/w by distillation of the IPAC at 45° C. under vacuum. 49.8 g of 98% w/w ZnCl$_2$, 45 g of acetic acid, 4.6 g of 36% w/w hydrochloric acid and then 4.8 g of water are added to the suspension obtained. The reaction medium is heated to 62° C. 161.6 g of 91.6% w/w isophytol are then run in over 60 min. After the isophytol has finishing being run in, the reaction is maintained at 62° C. for 50 min. 100 g of water are charged with stirring and the mixture is subsequently separated by settling. A second washing is carried out with 60 g of water. In all, 269.7 g of aqueous phase comprising 100 g of water and 12 g of 50% NaOH. The organic phase is evaporated on a rotary evaporator at 60° C. under vacuum for 2 h.

After evaporation and partial purification, 237.8 g of 96% w/w tocopheryl acetate (Toco) are obtained (yield=97%).

The aqueous phase (269.7 g), comprising ZnCl$_2$ and HCl, is evaporated on a rotary evaporator under a vacuum of 5 to 10 torr at approximately 115° C. until a suspension is obtained (~90% w/w of ZnCl$_2$). 45.6 g of AcOH are added to this suspension in order to obtain a solution. The exact ZnCl$_2$ assay is quantitatively determined by colorimetry. This ZnCl$_2$ solution is used in the following TMHQ/Isophytol condensation reaction, where the additional water charge is no longer necessary. The amounts of reactants (TMHQ, 36% HCl and isophytol) are calculated on the basis of the amount of ZnCl$_2$ recycled, so as to maintain a ZnCl$_2$/Isophytol molar ratio of 0.72 eq.

The procedures of Examples 21 to 23 are identical to that of Example 20.

TABLE 5

Recycling of ZnCl$_2$.

| Example | Recycling | Maintenance time (min) | AcOH (g) | TMHQ (eq) | ZnCl$_2$ (eq)* | Acid (eq) | T (° C.) | Total H$_2$O** (mol/mol ZnCl$_2$) | Toco assay (%) | Toco Yd (% pure/pure) |
|---|---|---|---|---|---|---|---|---|---|---|
| 20 | 0 | 50 | 45 | 1.01 | 0.73 | 36% HCl (0.09) | 62 | 1.16 | 96*** | 97 |
| 21 | 1 | 50 | 45.6 | 1.01 | 0.73 | 36% HCl (0.09) | 62 | 1.14 | 95.6*** | 97.2 |
| 22 | 2 | 50 | 43.6 | 1.01 | 0.70 | 36% HCl (0.09) | 62 | 1.25 | 95.3*** | 97.2 |
| 23 | 3 | 50 | 42.75 | 1.01 | 0.68 | 36% HCl (0.09) | 62 | 1.34 | 95.8*** | 97.2 |

*the equivalents are in moles with respect to the number of moles of isophytol
**total H$_2$O = H$_2$O + H$_2$O present in the acid
***After partial purification more than 99.5% of the ZnCl$_2$ charged are recovered. The volatile products are removed from the organic phase by distillation at 75° C. under vacuum. 0.7 g of 92% w/w sulphuric acid are charged at 70° C. and then 68 g of 92% w/w acetic anhydride are run in at this temperature over 10 min. The reaction medium is maintained at this temperature for 90 min and then rapidly cooled to 35° C. 240 g of hexane are charged with stirring, followed by 220 g of water and by 9 g of 92% w/w H$_2$SO$_4$. The two phases are separated by settling. The organic phase is then washed with a mixture of Acetylation Catalysts: Influence on the Coloration of the Tocopheryl Acetate (Toco)

Examples 24 to 26

The procedure and the charges of the TMHQ/Isophytol condensation are identical to those in Example 16.

Only the acetylation stage is changed. The parameters are shown in Table 6.

TABLE 6

Influence of the acetylation catalyst on the Toco coloration

| Example | Catalyst | Cata. eq. (mol %) | Ac₂O (g) | T (° C.) | Time for running in Ac₂O (min) | Maintenance time (min) | Toco assay (%) | Toco Yd (% pure/pure) |
|---|---|---|---|---|---|---|---|---|
| 24 | 92% H₂SO₄ | 2 | 1.3 | 70 | 7 | 90 | 89.9 | 97.5 |
| 25 | 85% H₃PO₄ | 2 | 1.3 | 95 | 7 | 90 | 89.14 | 96.6 |
| 26 | AcONa | 10 | 1.3 | 110 | 7 | 90 | 89.43 | 98.6 |

The Toco colorations in solution were measured by the Gardner method.

The Toco samples were diluted in cyclohexane. The solution is introduced into a 10 mm quartz cell. The analysis is carried out in the 400–700 nm spectral range.

The trichromatic coordinates are as follows:

| Catalyst | x | y | Y |
|---|---|---|---|
| H₂SO₄ | 0.5452 | 0.4325 | 0.84 |
| H₃PO₄ | 0.4553 | 0.4596 | 40.67 |
| AcONa | 0.4424 | 0.4594 | 67.71 |

The representation of these points on the corresponding Gardner curve is as follows:

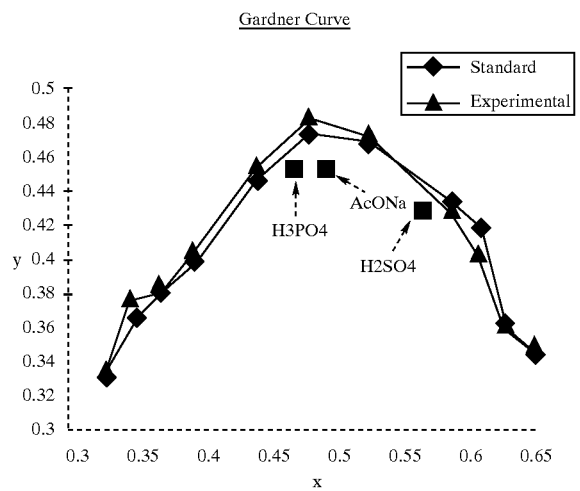

The curve shows that $H_3PO_4$ and acona result in products which are less coloured than $H_2SO_4$.

What is claimed is:

1. Process for preparing α-tocopherol by the condensation of a phytol with trimethylhydroquinone in a polar solvent of the ester type and in the presence of a Bronsted acid and of a zinc halide, characterized in that the reaction is carried out in the presence of an amount of water of between 0.7 molar eq. and 2 molar eq. with respect to the number of moles of zinc halide used and in the presence of an amount of zinc halide of greater than 0.3 molar equivalent with respect to the phytol.

2. Process according to claim 1 characterized in that the amount of zinc halide is between 0.7 and 1.2 molar eq. with respect to the phytol.

3. Process according to claim 1, characterized in that the zinc halide is zinc chloride.

4. Process according to claim 1, characterized in that the solvent is selected from alkyl acetates comprising 2 to 4 carbon atoms in the alkyl chain.

5. Process according to claim 1, characterized in that the Bronsted acid is selected from hydrochloric acid or sulphuric acid.

6. Process according to claim 5, characterized in that the molar amount of Bronsted acid is between 4% and 16% with respect to the number of moles of phytol.

7. Process according to claim 1, characterized in that an organic acid is added to the reaction medium.

8. Process according to claim 7, characterized in that the amount by weight of organic acid used is between 3 and 20 times the amount by weight of water present in the medium.

9. Process for the preparation of α-tocopherol acetate, characterized in that the α-tocopherol is brought into contact with acetic anhydride in the presence of an inorganic acid chosen from sulphuric acid or phosphoric acid or in the presence of an alkaline acetate and in the absence of any solvent.

10. Process according to claim 9, characterized in that use is made of 0.7 to 2 molar % of acid as acetylation catalyst when the latter is sulphuric acid, 1 to 2 molar % when the acetylation catalyst is phosphoric acid and 5 to 10 molar % when the acetylation catalyst is sodium acetate.

11. A process according to claim 7, characterized in that the organic acid is acetic acid.

* * * * *